(12) United States Patent
Jensen et al.

(10) Patent No.: US 9,478,026 B2
(45) Date of Patent: Oct. 25, 2016

(54) SYSTEMS AND METHODS FOR DETERMINING WHITE MATTER FIBER TRACTOGRAPHY

(71) Applicants: MUSC Foundation for Research Development, Charleston, SC (US); Golbarg Tarighat Saber, Charleston, SC (US)

(72) Inventors: Jens Jensen, Charleston, SC (US); Ali Tabesh, Charleston, SC (US); Joseph Helpern, Sullivans Island, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 14/673,991

(22) Filed: Mar. 31, 2015

(65) Prior Publication Data

US 2015/0279029 A1  Oct. 1, 2015

Related U.S. Application Data

(60) Provisional application No. 61/972,559, filed on Mar. 31, 2014.

(51) Int. Cl.
| | |
|---|---|
| *G06T 7/00* | (2006.01) |
| *A61B 5/00* | (2006.01) |
| *A61B 5/16* | (2006.01) |
| *A61B 5/055* | (2006.01) |
| *G01R 33/563* | (2006.01) |

(52) U.S. Cl.
CPC ........... *G06T 7/0012* (2013.01); *A61B 5/0042* (2013.01); *A61B 5/055* (2013.01); *G01R 33/56341* (2013.01); *G06T 7/0081* (2013.01); *A61B 5/168* (2013.01); *A61B 5/4088* (2013.01); *A61B 5/4094* (2013.01); *A61B 2576/026* (2013.01); *G06T 2207/10092* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 8,811,706 B2 | 8/2014 | Jensen et al. | |
| 2012/0002851 A1* | 1/2012 | Jensen | G01R 33/56341 382/128 |
| 2015/0055845 A1 | 2/2015 | Jensen et al. | |

OTHER PUBLICATIONS

Jensen JH, Helpern JA, Diffusional kurtosis imaging: the quantification of non-Gaussian water diffusion by means of magnetic resonance imaging. Magn Reson, Med 2005; 53:1432-1440.*
Andrew L. Alexander, Diffusion Tensor Imaging of the Brain, Americal Society for Experimental Neuro Therapeutics Inc, col. 4, 316-329, Jul. 2007.*

* cited by examiner

*Primary Examiner* — Siamak Harandi
*Assistant Examiner* — Pinalben Patel
(74) *Attorney, Agent, or Firm* — Tarolli, Sundheim, Covell & Tummino LLP

(57) ABSTRACT

One aspect of the present disclosure relates to a system that can determine a kurtosis diffusion orientation distribution function (dODF) that can, for example, be used with diffusional kurtosis imaging fiber tractography (DKI-FT). The system can include a non-transitory memory storing computer-executable instructions and a processor that executes the computer-executable instructions to perform the following operations. Diffusion magnetic resonance imaging (dMRI) data can be received. Based on the dMRI data, a diffusion tensor (DT) and a diffusional kurtosis tensor (DKT) can be determined. A kurtosis dODF can be determined for the dMRI data based on the DT and the DKT. The kurtosis dODF extends a Gaussian approximation of the DT to include non-Gaussian corrections of the DKT.

18 Claims, 13 Drawing Sheets

SYSTEMS AND METHODS FOR DETERMINING WHITE MATTER FIBER TRACTOGRAPHY

RELATED APPLICATION

This application claims the benefit of U.S. Provisional Patent Application No. 61/972,559, filed Mar. 31, 2014, entitled "SYSTEMS AND METHODS FOR IMAGING USING DIFFUSIONAL ORIENTATION DISTRIBUTION FUNCTIONS," the entirety of which is hereby incorporated by reference for all purposes.

GOVERNMENT SUPPORT

This invention was made with government support under 1R01AG027852 and 1R01EB007656 awarded by the NIH and EPS-0919440 awarded by the NSF/EPSCoR. The government has certain rights in the invention.

TECHNICAL FIELD

The present disclosure relates generally to systems and methods for determining white matter fiber tractography (WMFT) and, more specifically, to systems and methods employing diffusional kurtosis imaging fiber tractography (DKI-FT) to determine the WMFT of an object in a magnetic resonance imaging (MRI) image.

BACKGROUND

White matter fiber tractography (WMFT) refers to a class of techniques that use data obtained with diffusion magnetic resonance imaging (dMRI) to map axonal fiber bundles within white matter of the brain. WMFT, which can be obtained in three dimensions for the whole brain in vivo in a completely noninvasive manner, has revolutionized the study of structural brain connectivity. In fact, WMFT is being used clinically for the planning of neurosurgical interventions so that surgeons can preserve critical brain functions. However, the various WMFT techniques differ in accuracy and practicality.

Human applications in clinical settings have favored a technique based on diffusion tensor imaging (DTI), referred to as DTI fiber tractography (DTI-FT). While DTI-FT is readily implemented on standard clinical magnetic resonance imaging (MRI) scanners, DTI-FT suffers from substantial inaccuracies because it is incapable of detecting the intersection of two or more fiber bundles within an imaging voxel. This so-called "fiber crossing problem" has led to the development of several alternative WMFT approaches. However, due to various challenges with implementation, these approaches have not replaced DTI-FT for most clinical applications.

SUMMARY

To overcome these challenges, the present disclosure relates generally to systems and methods for determining white matter fiber tractography (WMFT) and, more specifically, to systems and methods for using diffusional kurtosis imaging fiber tractography (DKI-FT) to determine the WMFT of an object in a magnetic resonance imaging (MRI) image. DKI-FT can expose fiber crossings unseen with traditional mechanisms (e.g., diffusion tensor imaging fiber tractography (DTI-FT)) with a high sensitivity. Additionally, DKI-FT can exhibit an efficient calculation scheme, allowing DKI-FT to be implemented in clinical applications.

In one aspect, the present disclosure can include a system including a non-transitory memory storing computer-executable instructions and a processor that executes the computer-executable instructions. Upon execution of the computer-executable instructions, diffusion magnetic resonance imaging (dMRI) data can be received. For example, the dMRI data can include at least a portion of a subject's brain. Based on the dMRI data, a diffusion tensor (DT) and a diffusional kurtosis tensor (DKT) can be determined. A kurtosis diffusion orientation distribution function (dODF) can be determined for the dMRI data based on the DT and the DKT. The kurtosis dODF extends a Gaussian approximation of the DT to include non-Gaussian corrections of the DKT. The kurtosis dODF can be used in DKI-FT to determine WMFT of the dMRI data.

In another aspect, the present disclosure can include a method that can be performed by a system that includes a processor. The method can include receiving dMRI data. For example, the dMRI data can include at least a portion of a subject's brain. A DT and a DKT can be determined for the dMRI data. Based on the DT and the DKT, a kurtosis dODF can be determined for the dMRI data. The kurtosis dODF can extend a Gaussian approximation of the DT to include non-Gaussian corrections of the DKT. The kurtosis dODF can be used in DKI-FT to determine WMFT of the dMRI data.

In a further aspect, the present disclosure can include a non-transitory computer-readable storage medium storing instructions executable by an associated processor to perform operations. The operations can include receiving dMRI data of at least a portion of a subject's brain and determining by the system, a kurtosis dODF for the dMRI data. The kurtosis dODF ($\psi_{\alpha,K}(\hat{n})$) can be represented by the following equation:

$$\psi_{\alpha,K}(\hat{n}) = \psi_{\alpha,G}(\hat{n})\left\{1 + \frac{1}{24}\sum_{i,j,k,l}\left[\frac{3U_{ij}W_{ijkl}U_{kl} - 6(\alpha+1)U_{ij}W_{ijkl}V_{kl} +}{(\alpha+1)(\alpha+3)V_{ij}W_{ijkl}V_{kl}}\right]\right\},$$

$$\text{where } V_{ij} \equiv \frac{(U\hat{n})_i(U\hat{n})_j}{\hat{n}^T U\hat{n}},$$

wherein $\psi_{\alpha,G}(\hat{n})$ represents the Gaussian dODF, U represents a dimensionless tensor equal to the product of the mean diffusivity and the inverse of the DT, W represents the DKT, $\alpha$ represents a radial weighting power, i, j, k, and l are indices carried out from 1 to 3, and $\hat{n}$ is a unit direction vector. The kurtosis dODF can be used in DKI-FT to determine WMFT of the dMRI data.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
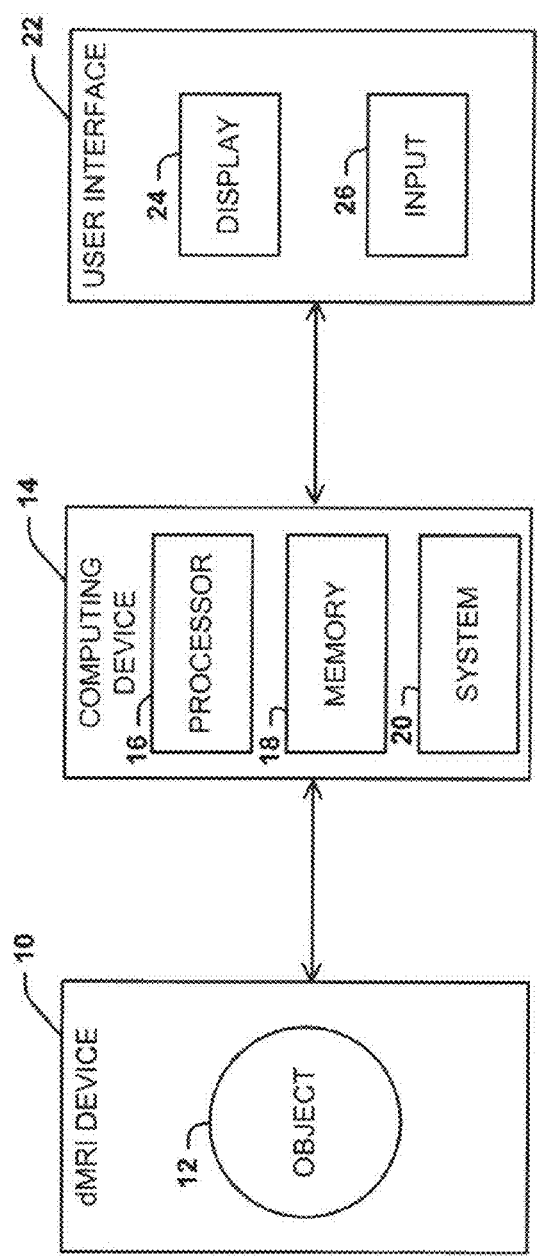
FIG. 1 shows a block diagram illustrating an example of a diffusional magnetic resonance imaging (dMRI) system that can be used to perform aspects of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

The sequence of operations (or acts/steps) is not limited to the order presented in the claims or figures unless specifically indicated otherwise.

As used herein, the term "diffusion magnetic resonance imaging", or "dMRI", can refer to a magnetic resonance imaging method that measures the diffusion of water molecules in biological tissues. When used here, the terms "magnetic resonance imaging" and "MRI" can refer to dMRI, unless otherwise stated. Diffusion MRI techniques allow for the diffusion to be measured both in vivo and non-invasively. For example, diffusion patterns of water molecules can reveal microscopic details about tissue architecture (e.g., information about a disease state). The diffusion anisotropy of water in biological tissues can be quantified with the "diffusion tensor", or "DT", which can describe the diffusion displacement probability using a Gaussian distribution function.

As used herein, the term "DT imaging", or "DTI", can refer to a dMRI technique that uses a Gaussian approximation for the displacement probability distribution governing the random displacement of water molecules. In biological tissue, however, the displacement probability distribution can deviate considerably from the Gaussian form.

As used herein, the term "diffusional kurtosis", or "DK", can refer to a quantitative measure of the degree to which the displacement probability distribution deviates from the Gaussian form. In other words, the diffusion anisotropy of water in biological tissues can be quantified with the "diffusional kurtosis tensor", or "DKT", which can describe the diffusion displacement probability using a non-Gaussian distribution function.

As used herein, the term "diffusional kurtosis imaging", or "DKI", can refer to a MRI technique (e.g., dMRI) that is an extension of DTI and can measure the diffusional kurtosis, which can be used to characterize tissue microstructure and provide information related to microscopic (e.g., intravoxel) diffusional heterogeneity.

As used herein, the term "white matter fiber tractography", "WMFT", or "FT", can refer to a class of techniques that use data obtained with dMRI to map axonal fiber bundles within white matter of the brain. One such technique can employ DTI for WMFT ("DTI-FT"). DTI-FT can determine the WMFT using only Gaussian contributions to the diffusion orientation distribution function (dODF). Another such technique can employ DKI for WMFT ("DKI-FT"). DKI-FT can determine the WMFT using both Gaussian and non-Gaussian contributions to the dODF. In some instances, WMFT can be used in the study, diagnosis, and treatment of different neurological disorders.

As used herein, the term "neurological disorder" can include diseases and disorders of the central nervous system (e.g., the brain and spinal cord). Examples of such neurological disorder can include Alzheimer's disease, attention deficit hyperactivity disorder, epilepsy, head trauma, schizophrenia, brain cancer, stroke, etc.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "subject" and "patient" can be used interchangeably herein.

As used herein, the term "object" can refer to at least a portion of a subject. For example, the object can correspond to the portion of the subject that is being imaged.

II. Overview

The present disclosure relates generally to systems and methods for determining white matter fiber tractography (WMFT) of an object in a magnetic resonance imaging (MRI) image. Traditionally, WMFT can be obtained using diffusion tensor imaging (DTI) fiber tractography (DTI-FT). While DTI-FT can be readily implemented on standard clinical magnetic resonance imaging (MRI) scanners, DTI-FT suffers from substantial inaccuracies. These inaccuracies can be due to the fact DTI-FT is incapable of detecting the intersection of two or more fiber bundles within an imaging voxel (the so called "fiber crossing problem").

To solve the fiber crossing problem, the present disclosure describes systems and methods that can determine the WMFT using diffusional kurtosis imaging fiber tractography (DKI-FT). DKI-FT incorporates both the Gaussian contributions of the diffusion tensor (DT) and the non-Gaussian approximation of the diffusional kurtosis tensor (DKT). DKI-FT is advantageous over conventional DTI-FT at least because it can predict the orientations of the fiber bundles more accurately, especially in areas like the centrum semiovale, where fiber crossings are common. The addition of the non-Gaussian contributions can contribute to resolution of intra-voxel fiber crossings. Unlike previous failed alternatives to DTI-FT, DKI-FT presents a clinically feasible alternative to DTI-FT because it can be implemented on standard clinical dMRI systems. Additionally, DKI-FT can provide a substantially better characterization of brain tissue diffusion properties, revealing axonal tracts that are invisible with DTI-FT. However DKI-FT still maintains the advantages of DTI-FT with regard to short data acquisition time and relatively simple and easy to implement analysis technique with a more efficient calculation scheme (using a simple, algebraic equation).

III. Systems

One aspect of the present disclosure can include a system that can use diffusional kurtosis imaging fiber tractography (DKI-FT) to determine the white matter fiber trajectory (WMFT) of an object in a diffusional magnetic resonance imaging (dMRI) image. The system can provide a clinically feasible solution that can resolve intersecting fiber bundles, solving the so-called fiber crossing problem. DKI-FT can generate a WMFT that, for example, can be used in surgical planning to help surgeons preserve critical brain functions. Additionally, the WMFT generated by DKI-FT can be used to quantitatively evaluate the structural connectivity of the brain, providing new biomarkers for various neurological disorders.

FIG. 1 illustrates a system that can use DKI-FT to determine the WMFT of an MRI image. The system of FIG. 1 is illustrated as a block diagram with the different blocks representing different components. For example, the components of the system of FIG. 1 can include a dMRI device 10, a computing device 14, and a user interface 22.

The dMRI device 10 can be configured to capture an image (hereinafter, the term "image" can include a single image or a sequence of images) of an object 12 and send the image to the computing device 14 for further processing. In some instances, the dMRI device 10 can capture an anatomical function of the object 12 in the image. For example, the anatomical function can be diffusion within the object 12. The object 12 can, for example, be brain tissue, kidney tissue, liver tissue, heart tissue, and/or any other bodily tissue of a subject. In the example described herein, the object 12 is brain tissue of the subject; however, other types of objects are not excluded.

The computing device 14 can be configured to process the image to determine a WMFT of the object 12 based on the image. The computing device 14 can include a processor 16, a non-transitory memory 18, and a system 20 for determining the WMFT of the object 12. The functions of system 20 can be implemented by computer program instructions that are stored in the non-transitory memory 18 and executable by the processor 16 to cause a series of operational steps to be performed to determine the WMFT of the object 12.

The non-transitory memory 18 can include any computer-usable or computer-readable storage medium that is not a transitory signal and can contain or store the program for execution by the processor 16. Examples of the non-transitory computer-readable storage medium can include an electronic, magnetic, optical, electromagnetic, infrared, or semiconductor system, apparatus or device. More specific examples (a non-exhaustive list) of the computer-readable storage medium can include the following: a portable computer diskette; a random access memory; a read-only memory; an erasable programmable read-only memory (or Flash memory); and a portable compact disc read-only memory. The processor 16 can be, for example, a processor of a general purpose computer, special purpose computer, and/or other programmable data processing apparatus that can create a mechanism for implementing the functions of the system 20. For example, upon execution by the processor 16, the system 20 can determine the WMFT of the object 12 in the image. Additionally, the computing device 14 can send a signal to the dMRI device 10 with various parameters for functionality of the dMRI device.

The user interface 22 can include one or more display devices (display 24) and one or more input devices (input 26). The display 24 can display images from the dMRI device 10. In some instances, the images from the dMRI device 10 displayed by the display 24 can include the WMFT determined by system 20 and/or additional processing undertaken by the computing device 14. The input 26 can include one or more devices that can receive user input, such as, for example, a keyboard, a mouse, a microphone, etc. For example, the input 26 can provide parameters that the computing device 14 can send to the dMRI device 10. In another example, the input 26 can be related to the determination of the WMFT by system 20.

Figure 2:
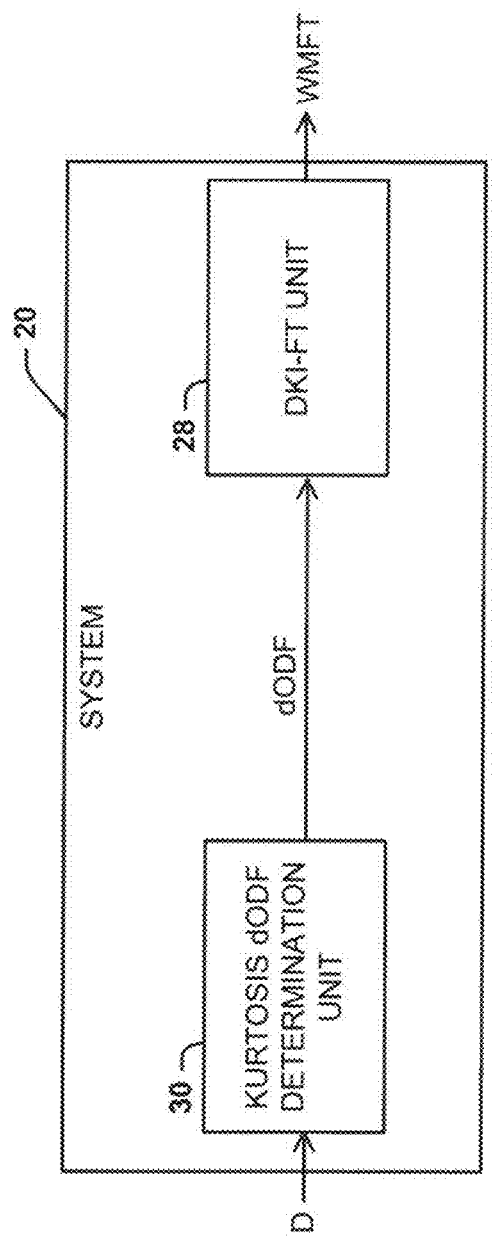
FIG. 2 shows a block diagram illustrating an example of a system that can determine a white matter fiber tractography (WMFT) of an object in an dMRI image obtained by the dMRI device in FIG. 1.

As shown in FIG. 2, in some examples, the system 20 of the computing device 14 can receive data (D) representing an image (e.g., from the dMRI device 10) and output a parameter related to the WMFT of the image. In certain aspects, system 20 can include a kurtosis dODF determination unit 30 and a DKI-FT unit 28. One or more of these components of system 20 can include instructions that are stored in the non-transitory memory 18 and executed by the processor 16. Each of the components can be in a communicative relationship with the other component, the processor 16, and/or the non-transitory memory 18 (e.g., via a direct or indirect electrical, electromagnetic, optical, or other type of wired or wireless communication) such that an action from the respective component causes an effect on the other component.

The kurtosis dODF determination unit 30 can receive the data (D) representing the image and determine at least one diffusion orientation distribution function (dODF) for the data (D). In some instances, the data (D) can include one or more raw signals obtained from or generated by the dMRI device 10 (e.g., including noise or other contaminant). In other instances, the data (D) can include one or more processed signals (e.g., with noise or another contaminant removed). Generally, the dODF is a convenient method for extracting directional information from the data (D). An important advantage of the dODF is that its calculation is not dependent on a specific model of tissue microstructure. However, the calculation of the dODF by the kurtosis dODF determination unit 30 does include both Gaussian and non-Gaussian contributions (taking into account the leading non-Gaussian corrections).

The DKI-FT unit 28 can receive the dODF and determine the WMFT based on the dODF. In some examples, the local maxima of the dODF, which depend on the Gaussian and non-Gaussian contributions, can indicate the directions of the axonal fiber bundles with a substantially improved accuracy compared to DTI-FT. Indeed, the accuracy can be improved due to the dependence on the non-Gaussian contributions, which can detect intersecting voxels within a voxel, thereby solving the fiber crossing problem.

Figure 3:
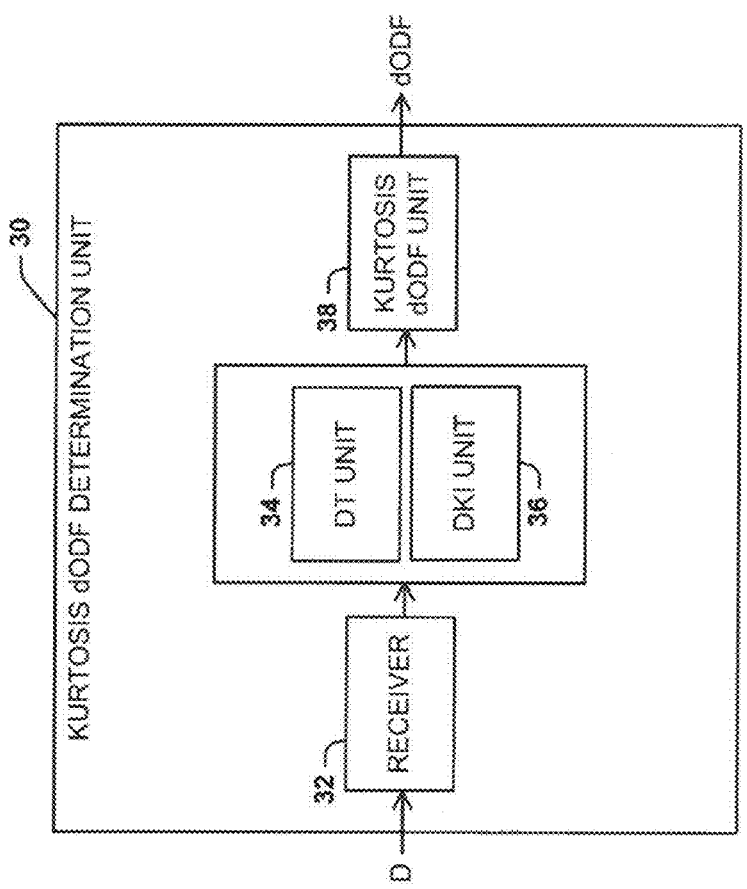
FIG. 3 shows a block diagram showing a kurtosis diffusion orientation distribution function (dODF) determination unit that can be part of the system in FIG. 2.

A more detailed example of the kurtosis dODF determination unit 30 is shown in FIG. 3. In this example, the kurtosis dODF determination unit 30 can include a receiver 32, a DT unit 34, a DKI unit 36, and a kurtosis dODF unit 38. Each of these components can be in a communicative relationship with another component, the processor 16, and/or the non-transitory memory 18 (e.g., via a direct or indirect electrical, electromagnetic, optical, or other type of wired or wireless communication) such that an action from the respective component causes an effect on another component.

The receiver 32 can receive the data (D). In some instances, the receiver 32 can perform one or more noise removal procedures on the data (D). Additionally, in other instances, the receiver 32 can adjust the data acquisition time of the dMRI device 10 to keep the image acquisition time to a minimum and/or to keep the size of the data (D) transmitted to the receiver 32 small. The receiver 32 can pass the data (D) (after any related processing) to the DT unit 34 and the DKI unit 36 for further processing to determine the kurtosis dODF from the data.

Generally, a class of dODFs can be determined by the radial integral:

$$\psi_\alpha(\hat{n}) \equiv \frac{1}{Z} \int_0^\infty s^\alpha \, ds P(s\hat{n}, t), \quad \text{Equation 1}$$

where $\psi_\alpha(\hat{n})$ is the dODF in a direction given by a unit direction vector $\hat{n}$, $P(s,t)$ is the water diffusion displacement probability density function (dPDF) for a molecular displacement s over a diffusion time t, and z is a normalization constant. The power $\alpha$ can affect the radial weighting of the dODF, with larger $\alpha$ corresponding to a greater sensitivity to long diffusion displacements. The dODF of Equation 1 does not make any explicit assumptions about tissue microstructure.

The DT unit 34 can determine the Gaussian dODF, which includes the Gaussian contributions to the dODF. To determine the Gaussian dODF, the diffusional average of an arbitrary function F(s) of the diffusion displacement s is given by:

$$\langle F(s) \rangle = \int d^3 s P(s,t) F(s), \quad \text{Equation 2}$$

where it is assumed that the dPDF is normalized so that:

$$1 = \int d^3 s P(s,t). \quad \text{Equation 3}$$

The components of the DT can then be expressed as:

$$D_{ij} = \frac{\langle s_i s_j \rangle}{2t}, \quad \text{Equation 4}$$

with $s_i$ indicating the components of s. The Gaussian approximation for the dPDF can be defined by:

$$P_G(s,t) \equiv \frac{1}{(4\pi t)^{3/2} |D|^{1/2}} \cdot \exp(-s^T D^{-1} s / 4t), \quad \text{Equation 5}$$

where D represents the DT (assumed to be positive and definite). It is this approximation that forms the basis of DTI. By combining Equations 1 and 5, the Gaussian dODF ($\psi_{\alpha,G}$) can be:

$$\psi_{\alpha,G}(\hat{n}) = \frac{1}{16 Z (\pi t)^{3/2} |D|^{1/2}} \cdot \Gamma\left(\frac{\alpha+1}{2}\right) \cdot \left(\frac{4t}{\hat{n}^T D^{-1} \hat{n}}\right)^{(\alpha+1)/2}, \quad \text{Equation 6}$$

where $\Gamma(x)$ is Euler's gamma function and a "G" has been added to the dODF symbol subscript to indicate that it is for the Gaussian approximation. Convergence of the integral in Equation 1 requires $\alpha > -1$.

Now a dimensionless tensor $U \equiv \bar{D} D^{-1}$ can be defined, where $\bar{D}$ is the mean diffusivity, and set the normalization constant to be:

$$Z = \frac{(4\bar{D}t)^{(\alpha+1)/2}}{16(\pi t)^{3/2} |D|^{1/2}} \cdot \Gamma\left(\frac{\alpha+1}{2}\right). \quad \text{Equation 7}$$

The Gaussian dODF then can take the simple from:

$$\psi_{\alpha,G}(\hat{n}) = \left(\frac{1}{\hat{n}^T U \hat{n}}\right)^{(\alpha+1)/2}. \quad \text{Equation 8}$$

When the Gaussian dODF is used to determine the WMFT, the eigenvectors of U coincide with those of the DT, and the maxima for the Gaussian dODF occur at $\hat{n} = \pm \hat{e}_1$, where $\hat{e}_1$ is the principal DT eigenvector, with the locations of the maxima independent of the radial weighting power $\alpha$.

The DKI unit 36 can determine the non-Gaussian contributions (or corrections) for the dODF. In order to systematically define non-Gaussian corrections for the dODF, it is helpful to introduce the Fourier transform of the dPDF:

$$\tilde{P}(q) = \int d^3 s P(s,t) e^{-2\pi i q \cdot s}, \quad \text{Equation 9}$$

where, for the sake of notational simplicity, explicit reference to the diffusion time in the arguments of $\tilde{P}$ has been suppressed. Because of the normalization condition of Equation 3, the following equation must be provided:

$$\tilde{P}(0) = 1. \quad \text{Equation 10}$$

In terms of $\tilde{P}$, the dODF can be written as:

$$\psi_\alpha(\hat{n}) = \frac{1}{Z}\int_0^\infty s^\alpha ds \int d^3q\, \tilde{P}(q)e^{2\pi i q\cdot s\hat{n}}. \qquad \text{Equation 11}$$

The corresponding Fourier transform for the Gaussian dODF is:

$$\tilde{P}_G(q) = \exp(-4\pi^2 t q^T D q), \qquad \text{Equation 12}$$

which is equivalent to the DTI approximation for the MRI signal as a function of the diffusion wave vector q.

One may construct an "η dependent" dODF so that:

$$\psi_{\alpha,\eta}(\hat{n}) \equiv \frac{1}{Z}\int_0^\infty s^\alpha ds \int d^3q\, \tilde{P}_G(q)\frac{\tilde{P}(\eta q)}{\tilde{P}_G(\eta q)}e^{2\pi i q\cdot s\hat{n}}. \qquad \text{Equation 13}$$

$$\psi_{\alpha,0}(\hat{n}) = \psi_{\alpha,G}(\hat{n}), \qquad \text{Equation 14}$$

and $$\psi_{\alpha,1}(\hat{n}) = \psi_\alpha(\hat{n}). \qquad \text{Equation 15}$$

Hence, the scaling parameter η provides a natural means for interpolating between the Gaussian and exact dODFs. The non-Gaussian corrections for the Gaussian dODF then can be systematically derived in terms of the Taylor series for $\psi_{\alpha,\eta}$ in powers of η about η=0. Assuming $\tilde{P}(q)=\tilde{P}(-q)$, the leading non-Gaussian corrections are of order $\eta^4$, and a direct calculation shows:

$$\frac{\psi_{\alpha,\eta}(\hat{n})}{\psi_{\alpha,G}(\hat{n})} = 1 + \frac{\eta^4}{24}\sum_{i,j,k,l}[3U_{ij}W_{ijkl}U_{kl} - 6(\alpha+1)U_{ij}W_{ijkl}V_{kl} + \qquad \text{Equation 16}$$

$$(\alpha+1)(\alpha+3)V_{ij}W_{ijkl}V_{kl}] + O(\eta^6),$$

where $U_{ij}$ indicates the components of U, $$V_{ij} \equiv \frac{(U\hat{n})_i(U\hat{n})_j}{\hat{n}^T U\hat{n}}, \qquad \text{Equation 17}$$

$W_{ijkl}$ are the components of the DKT, and the sums on the indices (i,j,l,k) are carried out from 1 to 3.

The kurtosis dODF unit 38 can determine the kurtosis dODF by dropping the terms of order $\eta^6$ and higher and setting η=1 in Equation 16.

$$\psi_{\alpha,K}(\hat{n}) = \qquad \text{Equation 18}$$

$$\psi_{\alpha,G}(\hat{n})\left\{1 + \frac{1}{24}\sum_{i,j,k,l}[3U_{ij}W_{ijkl}U_{kl} - 6(\alpha+1)U_{ij}W_{ijkl}V_{kl} + \right.$$

$$\left.(\alpha+1)(\alpha+3)V_{ij}W_{ijkl}V_{kl}]\right\},$$

which is the central result that extends the Gaussian approximation by including the leading non-Gaussian corrections. The expansion in the parameter η has been a formal device for organizing the non-Gaussian corrections, but for most specific models this would correspond, in essence, to an expansion for a physically well-defined parameter, often the ratio of a characteristic length scale for the microstructure to the diffusion length.

In order to better understand the physical meaning of the η expansion, first consider an example with:

$$\tilde{P}(q) = \tilde{P}_G(q)F(aq), \qquad \text{Equation 19}$$

where F(x) is an unspecified analytic function consistent with Equations 10 and 12, and a is a length that controls the diffusion wave vector scale at which non-Gaussian diffusion effects become apparent. Note that Equations 10 and 12 imply that F(0)=1. For this case, the expansion in η is equivalent to an expansion in a divided by the diffusion length $(2\overline{D}t)^{1/2}$, with $D/\overline{D}$ being kept fixed. The diffusion length enters here as the characteristic length scale for Gaussian diffusion.

As a second example, suppose:

$$\tilde{P}(q) = \tilde{P}_G(q)\sum_{m=1}^N f_m\exp(-4\pi^2 t q^T \delta D_m q), \qquad \text{Equation 20}$$

which corresponds to a model with N Gaussian compartments. Here $\delta D_m$ represents the difference between the DT of the $m^{th}$ compartment and the total DT. Consistency with Equation 10 implies that compartment weights, $f_m$, sum to unity. The spread may be quantified in compartmental diffusivities by:

$$\Delta D \equiv \left[\frac{1}{3}Tr\left(\sum_{m=1}^N f_m \delta D_m \delta D_m\right)\right]^{1/2}. \qquad \text{Equation 21}$$

The expansion in η can then be regarded as an expansion in $(\Delta D/\overline{D})^{1/2}$ with $D/\overline{D}$, $\delta D_m/\Delta D$ and $f_m$ being kept fixed.

Because of symmetry, $\psi_{\alpha,K}(\hat{n})=\psi_{\alpha,K}(-\hat{n})$ all isolated local maxima for the kurtosis dODF come in pairs related by point reflection through the origin. However, unlike the Gaussian dODF, the number of maxima pairs can exceed one, allowing fiber crossings to be resolved. The kurtosis dODF also differs from the Gaussian dODF in that the location of the maxima depend on the choice of α, and so the optimization of this parameter becomes of interest. Equation 18 is an explicit algebraic formula, rather than an integral.

IV. Methods

Figure 4:
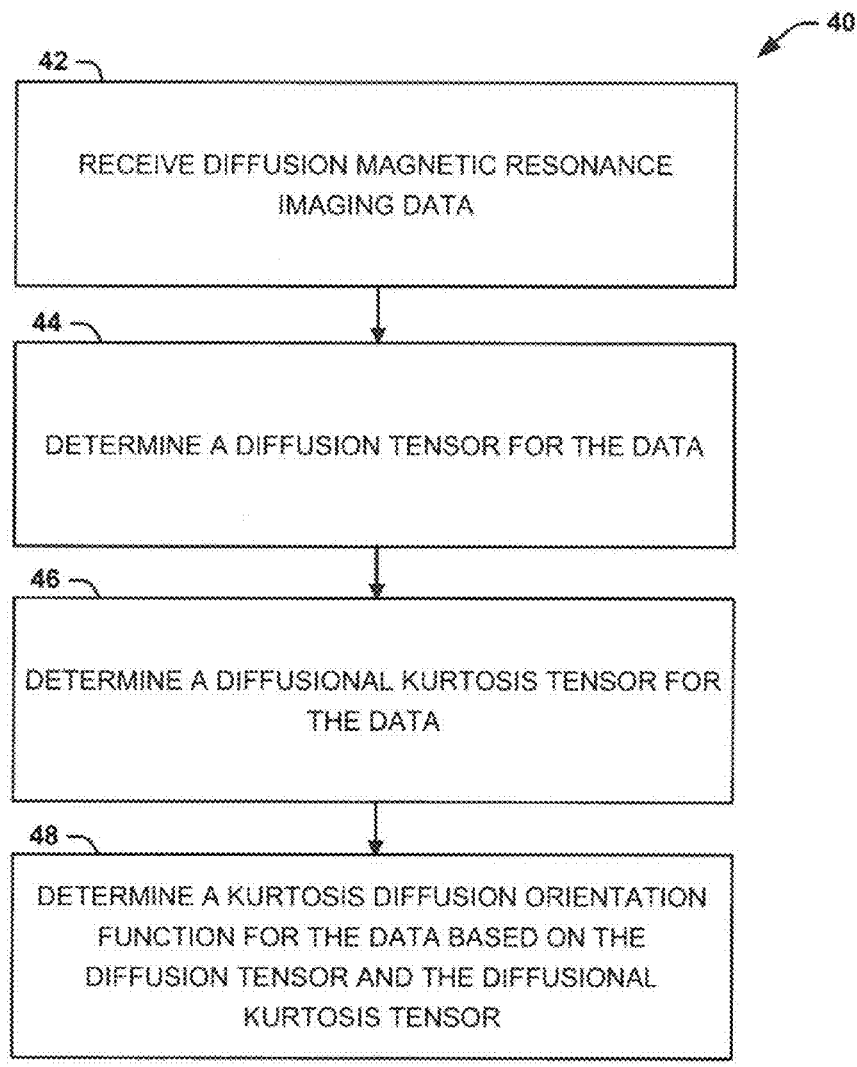
FIG. 4 shows a process flow diagram illustrating a method for determining kurtosis dODF of an object in a dMRI image in accordance with another aspect of the present disclosure.

Another aspect of the present disclosure can include methods for using diffusional kurtosis imaging fiber tractography (DKI-FT) to determine white matter fiber trajectory (WMFT) of a diffusional magnetic resonance imaging (dMRI) image. In one example, a system that is identically or similarly configured as described above in FIGS. 1-3 can be utilized to aid in determining the WMFT of a subject undergoing an MRI procedure and/or imaging study. In some instances, subject can be suspected of having a neurological disorder, such as: stroke, Alzheimer's disease, head trauma, schizophrenia, attention deficit hyperactivity disorder, etc. One example of a method 40 that can determine a kurtosis dODF for an object in a dMRI image is shown in FIG. 4. Another example of a method 50 that can determine a WMFT of the object in the dMRI image is shown in FIG. 5.

Figure 5:
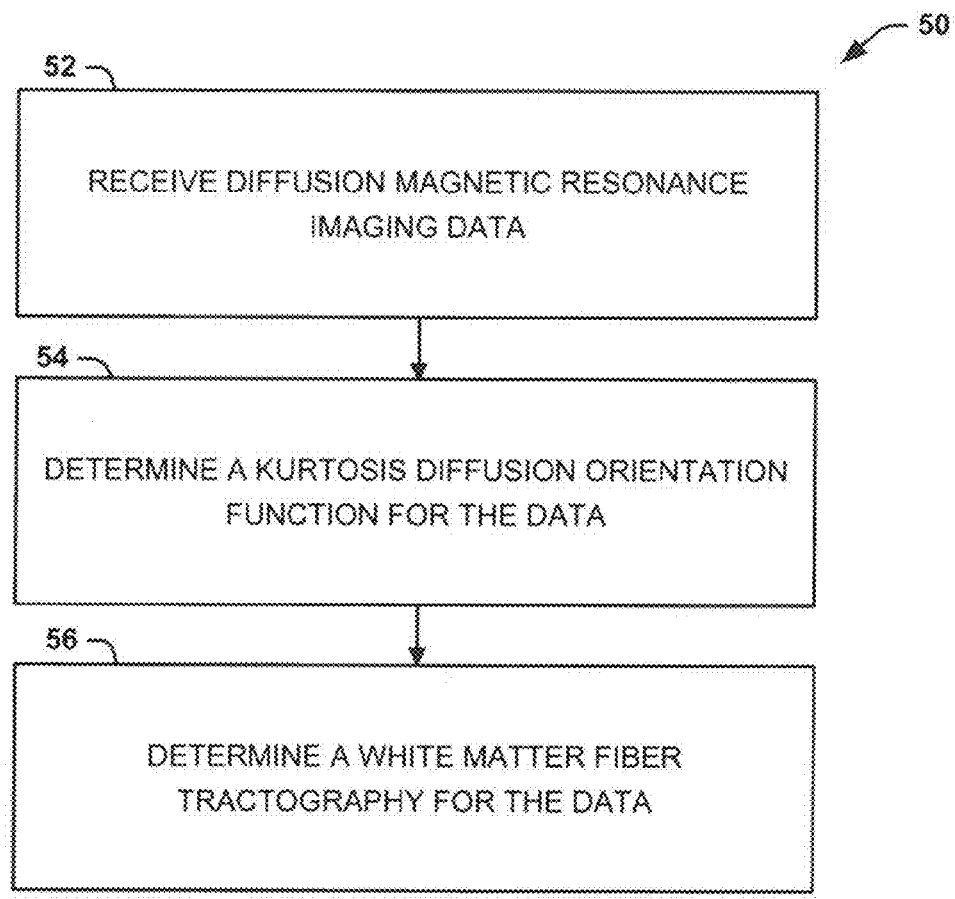
FIG. 5 shows a process flow diagram illustrating a method for determining a WMFT of the object in the dMRI image in FIG. 4.

The methods 40 and 50 of FIGS. 4 and 5, respectively, are illustrated as process flow diagrams with flowchart illustrations. For purposes of simplicity, the methods 40 and 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40 and 50.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 40 and 50 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the storage medium for use by or in connection with an instruction execution system. A computer-usable or computer-readable storage medium may be any non-transitory storage medium that can contain or store the program for use by or in connection with the instruction or execution of a system, apparatus, or device.

Referring to FIG. 4, another aspect of the present disclosure can include a method 40 for determining a kurtosis dODF for an object in a dMRI image. For example, a subject can undergo a dMRI imaging study where an image is obtained of an anatomical structure (e.g., all or only a portion of the subject's brain). At 42, image data can be received (e.g., by receiver 32 of the kurtosis dODF determination unit 30). At 44, a diffusion tensor (DT) can be determined for the data (e.g., by DT unit 34 of the kurtosis dODF determination unit 30). At 46, a diffusional kurtosis tensor (DKT) can be determined for the data (by DKI unit 36 of the kurtosis dODF determination unit 30). At 48, a kurtosis dODF can be determined for the data based on the DT and the DKT. For example, the kurtosis dODF can be determined according to the simple, algebraic Equation 18 (including Gaussian and non-Gaussian contributions).

Referring now to FIG. 5, another aspect of the present disclosure can include a method 50 for determining a WMFT of an object in an MRI image. Steps 52-54 are similar to steps 42-48 of the method 40 illustrated in FIG. 4. At 52, for example, dMRI data can be received (e.g., by receiver 32 of the kurtosis dODF determination unit 30) and, at 54, a kurtosis dODF can be determined for the data (e.g., by the kurtosis dODF determination unit 30). For example, the kurtosis dODF can be determined according to Equation 18.

At 56, a white matter fiber tractography (WMFT) can be determined for the object in the dMRI image (e.g., by DKI-FT unit 28) based on the kurtosis dODF. The WMFT can be displayed over the MRI image of the patient's brain with color corresponding to the tracts. In some instances, a medical condition can be evaluated based on the WMFT. For example, the progress or stage of the medical condition can be evaluated based on the WMFT.

V. EXAMPLE

The following example is for the purpose of illustration only and is not intended to limit the scope of the appended claims.

Example 1

This example illustrates an analytical representation of the leading non-Gaussian corrections for a class of diffusion orientation distribution functions (dODFs) that can be constructed using the diffusion tensor (DT) and the diffusional kurtosis tensor (DKT). To demonstrate the effects of the non-Gaussian corrections, experiments were completed that show that the inclusion of the leading non-Gaussian corrections, the results of which are presented below.

Methods

Two-Compartment Model

In order to illustrate and investigate the kurtosis approximation for the dODF, a simple two-component model of the crossing fibers was considered. The two-compartment model can be defined by:

$$\tilde{P}(q) = f\exp(-4\pi^2 tq^T D_A q) + (1-f)\exp(-4\pi^2 tq^T D_B q), \quad \text{Equation 22}$$

where $D_A$ and $D_B$ are the compartmental DTs and f is the relative water fraction for compartment A. These compartments may be regarded as representing two intersecting axonal fiber bundles within a single voxel.

For the DTs, the following were chosen:

$$D_A = \begin{pmatrix} \lambda_\| & 0 & 0 \\ 0 & \lambda_\perp & 0 \\ 0 & 0 & \lambda_\perp \end{pmatrix} \text{ and } \quad \text{Equation 23}$$

$$D_B = \begin{pmatrix} \lambda_\|\cos^2\xi + \lambda_\perp\sin^2\xi & (\lambda_\| - \lambda_\perp)\cos\xi\sin\xi & 0 \\ (\lambda_\| - \lambda_\perp)\cos\xi\sin\xi & \lambda_\|\sin^2\xi + \lambda_\perp\cos^2\xi & 0 \\ 0 & 0 & \lambda_\perp \end{pmatrix}. \quad \text{Equation 24}$$

The DT for compartment A models a fiber bundle oriented parallel to the x-axis with a principal eigenvalue $\lambda_\|$ while the DT for compartment B models a similar fiber bundle rotated in the xy-plane by an angle $\xi$. For numerical calculations, the values of $\lambda_\| = 2.0$ m²/ms and $\lambda_\perp = 0.4$ μm²/ms may be used, which are typical for white matter with high fractional anisotropy (FA).

The total DT for the model is:

$$D = fD_A + (1-f)D_B, \quad \text{Equation 25}$$

and the components of the DKT are:

$$W_{ijkl} = \frac{1}{\bar{D}^2}[f(D_{A,ij}D_{A,kl} + D_{A,ik}D_{A,jl} + D_{A,il}D_{A,jk}) + \quad \text{Equation 26}$$
$$(1-f)(D_{B,ij}D_{B,kl} + D_{B,ik}D_{B,jl} + D_{B,il}D_{B,jk}) -$$
$$D_{ij}D_{kl} - D_{ik}D_{jl} - D_{il}D_{jk}].$$

The Gaussian and kurtosis dODFs may then be calculated by using Equations 25 and 26 together with Equations 8 and 18.

The two-compartment DKT of Equation 26 will always yield a nonzero kurtosis for at least some directions unless $D_A = D_B$, f=0, or f=1. The model, thus, represents non-Gaussian diffusion for most parameter choices.

As illustrations, two main cases are examined. For the first case, f=0.8 is taken so that compartment A represents a dominant fiber bundle and compartment B represents a small admixture of a subdominant component. Ideally, the global maxima would correspond to the direction of the dominant bundle, and the departure is calculated from this (i.e., the angular error) given by the exact, Gaussian, and kurtosis dODFs for a range of $\xi$ and $\alpha$ values.

For the second case, f=0.5 is taken so that compartments A and B represent an intra-voxel crossing of two similar fiber bundles. While the Gaussian dODF is not able to resolve this crossing, the kurtosis dODF can if the crossing angle is not too small. For a range of $\xi$ and $\alpha$ values, the accuracy of the predicted direction for compartment A given by the maxima of the respective dODFs is determined.

Human Experiments

In order to illustrate the kurtosis dODF for normal brain, DKI data is obtained from one healthy volunteer (male, age 52). Briefly, a twice-refocused dMRI sequence is used with the imaging parameters: echo time=99 ms, repetition time=5300 ms, field of view=222×222 mm$^2$, acquisition matrix=74×74, voxel size=3×3×3 mm$^3$, number of slices=40, inter-slice gap=0 mm, bandwidth=1352 Hz/pixel, parallel imaging factor=2, b-values=0, 1000, 2000 s/mm$^2$, number of zero b-value images=6, number of gradient directions=30, number of averages=1, and total acquisition time=6 min, 46 s. This protocol was performed three times within the same scan session to test reproducibility and to allow for better signal averaging. The scans were obtained with a 3T MRI system (Tim Trio, Siemens Medical, Erlangen, Germany) using a 32-channel head coil under a protocol approved by the institutional review board of the Medical University of South Carolina.

Post-processing of raw diffusion-weighted images followed. To summarize, the diffusion-weighted images were skull-stripped, smoothed, co-registered and then globally fit to a standard DKI signal formula by means of constrained weighted linear least squares. Constraints were imposed on the diffusion parameters to keep them within prescribed limits as dictated by general physical properties (e.g., positive semi-definiteness of diffusion tensor eigenvalues), which helped to reduce the impact of signal noise. This data analysis utilized freely available software, referred to as Diffusional Kurtosis Estimator, and included calculation of parametric maps for the mean diffusivity (MD), FA, and mean kurtosis (MK). The precise correspondence between the dMRI signal and DKI parameters relies on an assumption of short gradient pulse durations. Although this condition is not strictly met for the dMRI sequence used in this study, as is typically the case for human dMRI, the effects of a long gradient pulse duration on DKI parameter estimates are likely to be small in brain.

Kurtosis dODFs were calculated on a voxel-by-voxel basis for $\alpha$=0, 2, and 4 by using Equation 18. The local maxima of these dODFs were determined by applying a quasi-Newton method utilizing the angular derivatives of the dODF with 100 initial points distributed on a uniform half-sphere grid. Distinct local maxima were then identified as the convergent solutions that were more than 1° apart from other local maxima. Locations of the maxima for the Gaussian dODFs were determined from the DT eigenvectors.

For the full DKI dataset (using the combined data from all three trials), the angular difference between the principal directions for the two dODFs, as indicated by the global maxima, was determined in each voxel, as well as the number of distinct fiber bundle directions identified in each voxel by the kurtosis dODF. For the voxels with 2 or more directions, the angles between the largest and second largest maxima of the kurtosis dODF were calculated, as an estimate of the fiber crossing angles. In order to test reproducibility, angular differences for the two dODFs and the number of directions detected by the kurtosis dODF were also calculated separately for the three individual trials. To suppress the confounding effects of cerebral spinal fluid, voxels with MD>1.5 μm$^2$/ms were excluded from analysis.

The Euler method was used to construct an elementary example of DKI-based fiber tractography (corresponding to the kurtosis dODF) for a single dataset. This was compared to DTI-based fiber tractography (corresponding to the Gaussian dODF) employing the same data, algorithm and seed region. To highlight the effect of voxels with crossing fibers, a seed region was selected within the centrum semiovale, a fiber crossing-rich white matter area where the superior longitudinal fasciculus, corpus callosum, and corona radiata intersect. A step size of 1 mm was used for the Euler method. Fiber termination criteria were FA<=0.1 and/or a change-of-direction >60°/mm. The radial weighting power $\alpha$ was set to 4 for the kurtosis dODF.

Results

Figure 6:
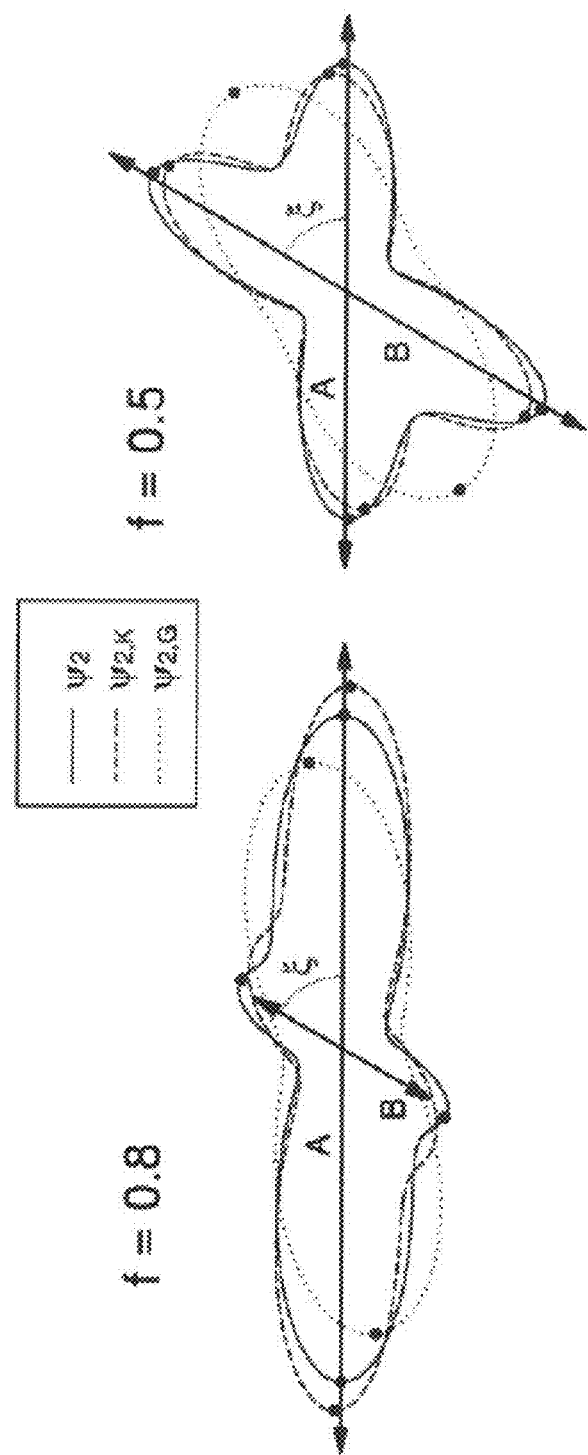
FIG. 6 shows plots in the xy-plane of the exact dODF (solid line), the kurtosis dODF (dashed line), and Gaussian dODF (dotted line) with f=0.8 and f=0.5 for a two-compartment model.

The exact, kurtosis, and Gaussian dODFs are shown in FIG. 6 for the two compartment model with $\alpha$=2 and $\xi$=60° for the two cases of f=0.8 and f=0.5. In both examples, the exact dODF accurately predicts the true directions of the fiber bundles. The Gaussian dODF yields only a single direction, which deviates substantially from either of the true directions. When f=0.8, the kurtosis dODF gives a good approximation for the direction of the dominant fiber bundle (angular error=−0.96°). When f=0.5, the kurtosis dODF detects the directions for both fiber bundles with an angular error of 4.78°.

Figure 7:
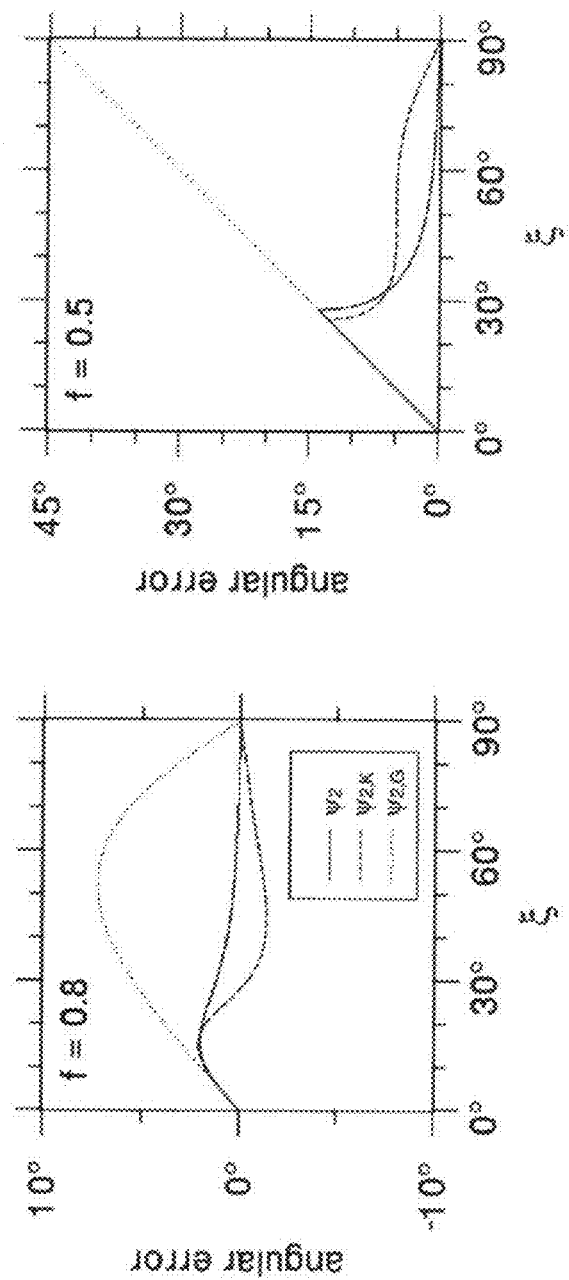
FIG. 7 shows plots of angular errors as a function of $\xi$ for $\alpha=2$ dODFs (exact, kurtosis, and Gaussian) with f=0.8 and with f=0.5 for the two-compartment model.

The angular errors for the predicted direction of fiber bundle A, as obtained from the maxima of the three $\alpha$=2 dODFs, are plotted in FIG. 7 as a function of the crossing angle $\xi$. When f=0.8, the exact dODF has a maximum error of 2.01° for $\xi$=16.1°, the Gaussian dODF has a maximum error of 7.24° for $\xi$=52.3°, and the kurtosis dODF has a maximum error of 2.11° for $\xi$=15.0°. When f=0.5, the exact dODF has a maximum error of 13.9° for $\xi$=27.8°, the Gaussian dODF has a maximum error of 45.0° for $\xi$=90.0°, and the kurtosis dODF has a maximum error of 12.8° for $\xi$=25.6°. In the case of f=0.5, the angular errors for all the dODFs are identical up to $\xi$=25.6°, as none of them are able to resolve the fiber crossing for these small intersection angles. Overall, the kurtosis dODF substantially improves upon the predictions of the Gaussian dODF.

Figure 8:
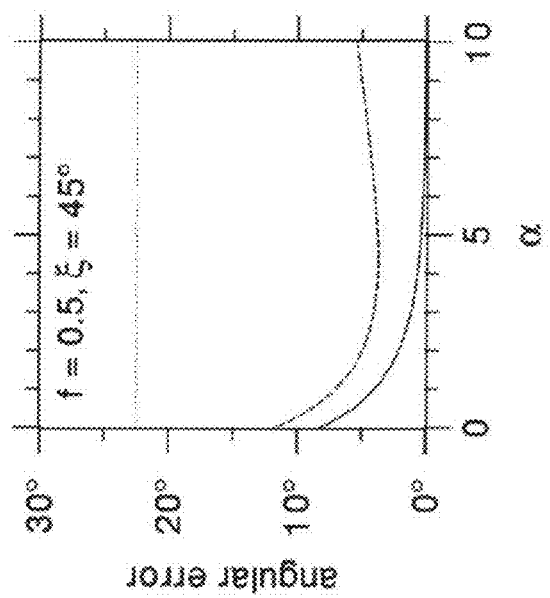
FIG. 8 shows plots of angular errors as a function of $\alpha$ for the dODFs (exact, kurtosis, and Gaussian) with f=0.8 and with f=0.5 for the two-compartment model.
Figure 8:
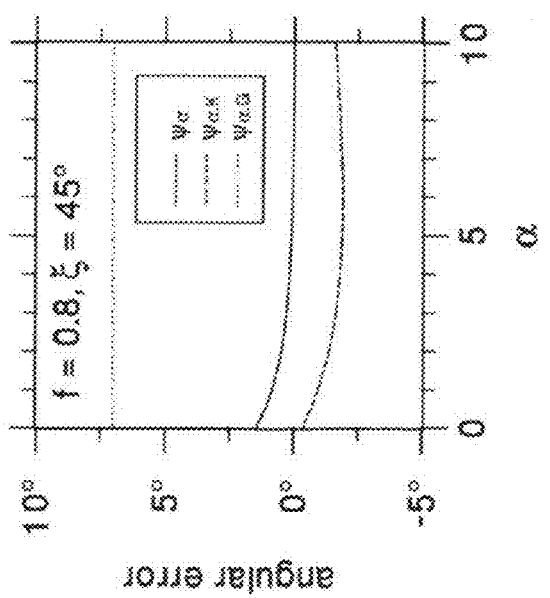

The dependence of the angular error as a function of the radial weighting power $\alpha$ is illustrated in FIG. 8 for the two-compartment model with $\xi$=45°. The exact dODF becomes more accurate as $\alpha$ is increased, while the accuracy of the Gaussian dODF is independent of $\alpha$. The kurtosis dODF depends on $\alpha$, but its accuracy does not necessarily improve monotonically. This suggests that there may be an optimal choice of $\alpha$ for the kurtosis dODF. Based on these results, the maximum $\alpha$ was set to 4 in the analysis of human data.

Figure 9:
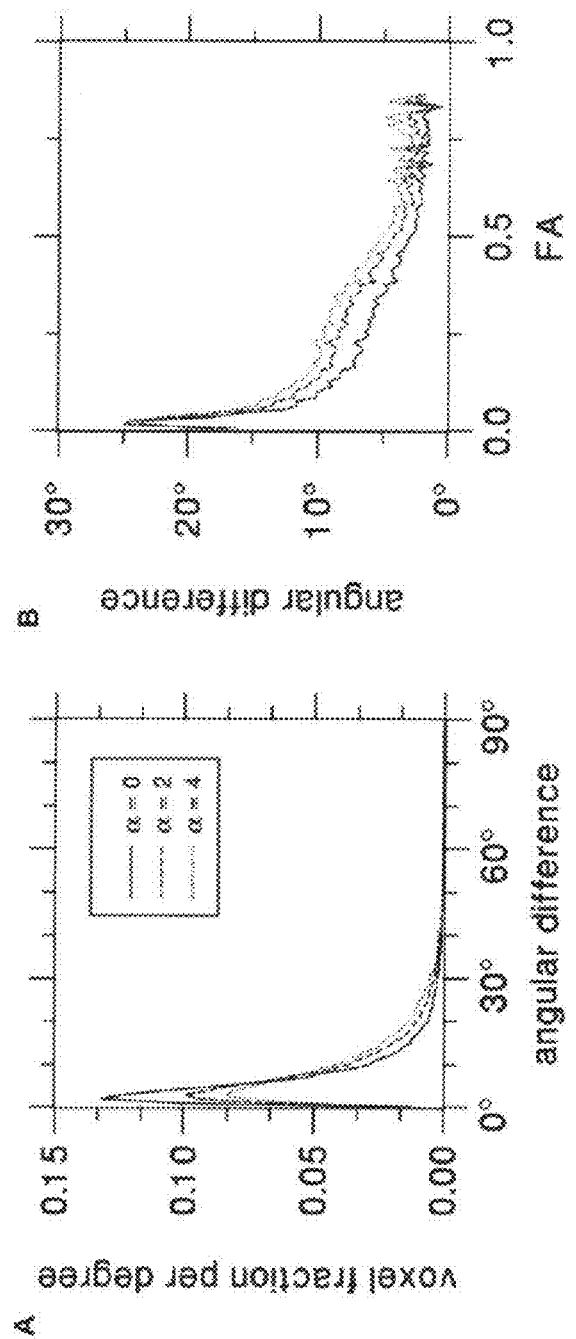
FIG. 9 shows plots of (A) a distribution of the absolute angular difference between the principal fiber direction identified with the Gaussian dODF and the primary direction estimated with the kurtosis dODF for human data and (B) the angular differences as a function of the FA values.

The distributions of angular differences between the Gaussian and kurtosis dODF global maxima, as obtained from the human data, are plotted in FIG. 9 for $\alpha$=0, 2, and 4. Also shown in FIG. 9 are the angular differences as a function of the fractional anisotropy (FA). For voxels with FA>0.2, the mean angular differences are 4.2° for $\alpha=0$, 6.0° for $\alpha=2$, and 7.2° for $\alpha=4$.

Figure 10:
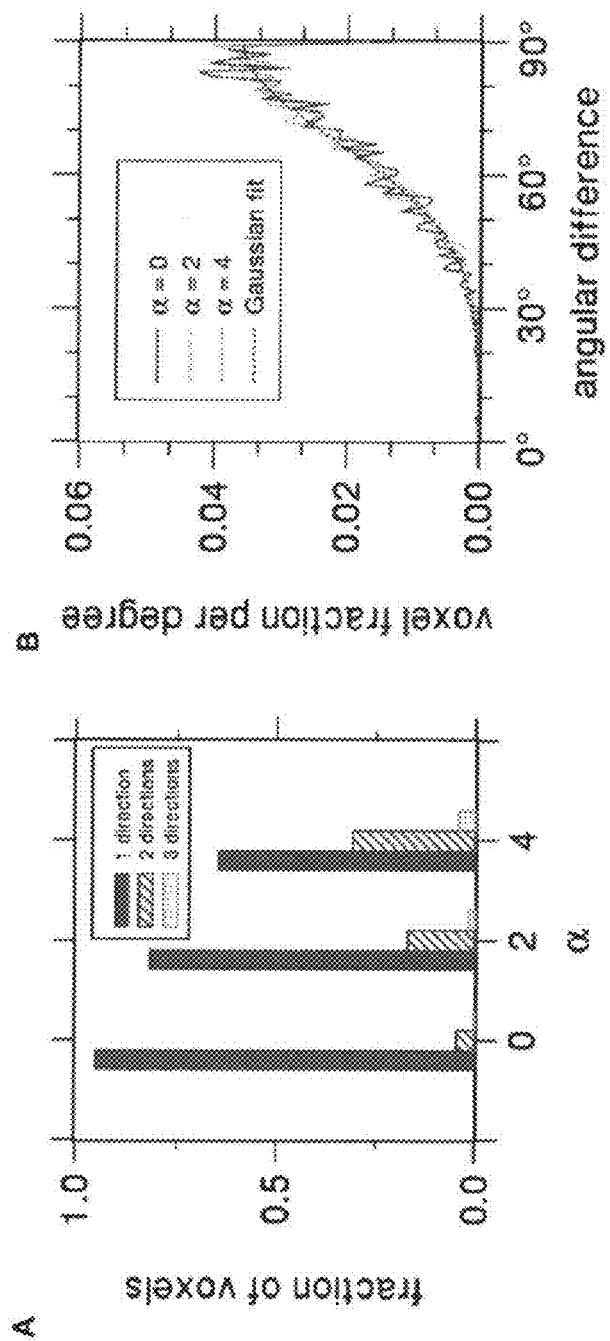
FIG. 10 shows plots of (A) a fraction of brain parenchyma voxels in which the kurtosis dODF detects 1, 2, or 3 fiber directions and (B) differences, for $\alpha=0$, 2, and 4, of the angular differences (with a bin size of 1°) between the directions identified by the largest maxima and the second largest maxima for all voxels with fractional anisotropy (FA)≥0.2 and in which 2 or more fiber directions are identified.

For the same DKI dataset and radial weighting powers, the fractions of voxels in which the kurtosis dODF identifies 1, 2, or 3 directions are given by FIG. 10. Most of the voxels have only one direction, but a substantial fraction has 2 or 3 suggesting the presence of intra-voxel fiber crossings. The fraction of voxels with detected crossings grows with increasing $\alpha$. Also shown in FIG. 10 are the distributions of the fiber crossing angles for voxels with 2 or more directions and with FA≥0.2. The crossing angles were estimated from the angular differences between the directions identified by the largest and second largest maxima of the kurtosis dODF. Interestingly, similar distributions are found for all three radial weighting powers. These distributions are well fit by a Gaussian function centered at a crossing angle of 90° and having a standard deviation of 22°.

Figure 11:
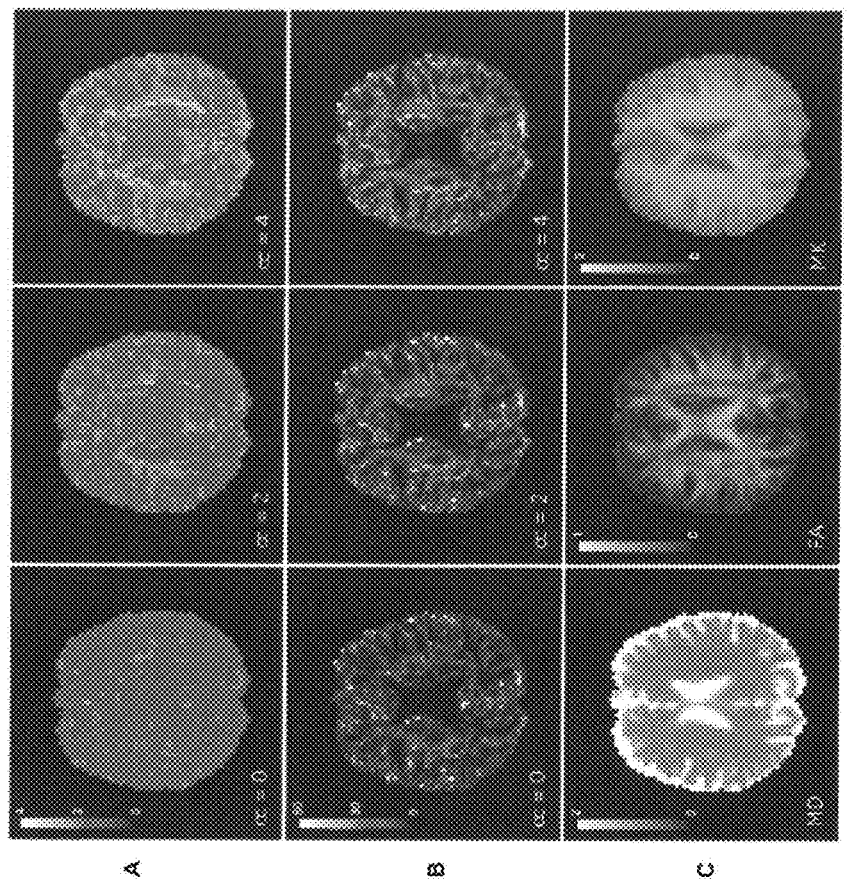
FIG. 11 shows maps of (A) the number of directions detected by the kurtosis dODF for $\alpha=0$, 2, and 4 from a single axial brain slice, (B) the angular differences between the principal directions, as identified by the global maxima of the Gaussian and kurtosis dODFs, with the scale bar being calibrated in degrees (colored voxels are again for mean kurtosis (MK)≥0.9 to highlight white matter regions), and (C) the corresponding maps of the mean diffusivity (MD), FA, and MK.

For a single axial slice, maps of the number of fiber crossings identified by the kurtosis dODF are displayed in FIG. 11, again demonstrating the greater sensitivity to fiber crossings for larger $\alpha$. For the same slice, FIG. 11 also gives maps of the angular difference between directions corresponding to the global maxima of the Gaussian and kurtosis dODFs. Substantial differences are seen in much of the white matter, indicating that the non-Gaussian corrections for the dODF are significant.

Figure 12:
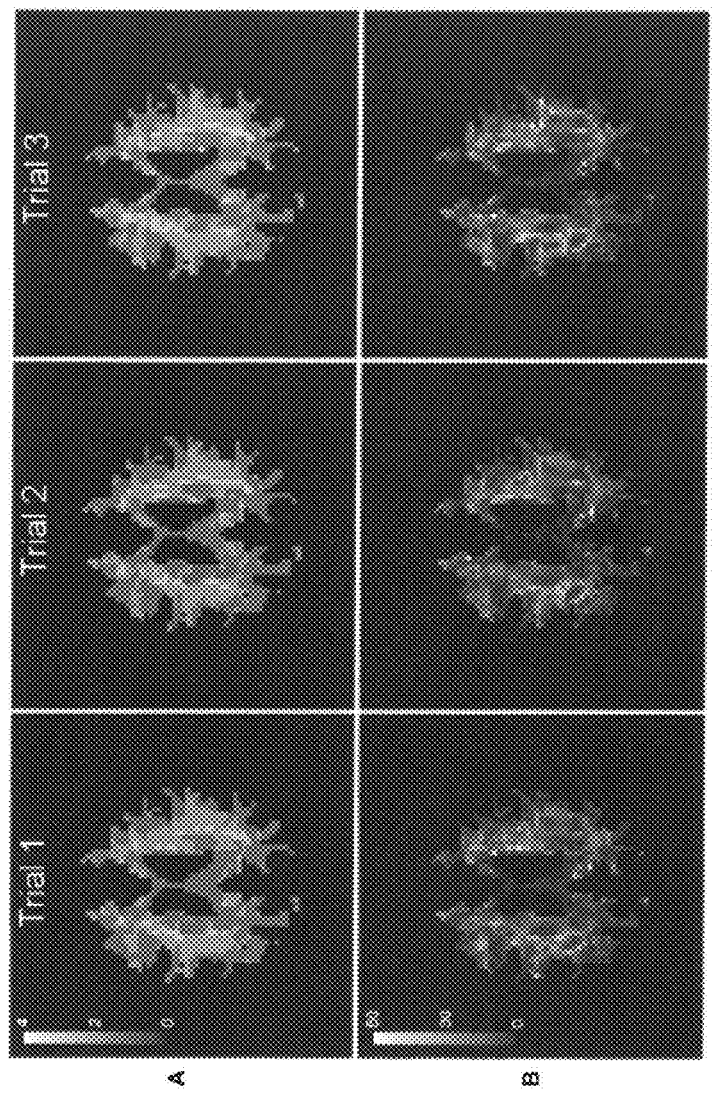
FIG. 12 shows maps of (A) white matter voxels detected by the kurtosis dODF ($\alpha=4$) and (B) corresponding maps of the angular differences between the directions identified by the global maxima of the Gaussian and kurtosis dODFs (scale bar is calibrated in degrees)

Maps for the number of detected fiber crossings and the Gaussian/kurtosis dODF angular differences are presented by FIG. 12, as calculated separately for the three individual trials with $\alpha=4$. Only voxels from white matter regions, defined as MK≥0.9, are displayed, since the results for gray matter largely reflect noise due to gray matter's low degree of diffusional anisotropy. That similar maps are obtained in each case supports the reproducibility of dODF calculations. White matter segmentation used the mean kurtosis (MK) rather than the FA, since the FA is low in both gray matter and in white matter regions with fiber crossings. The MK threshold of 0.9 was based on data of Falangola and coworkers reported in Falangola et al. Age Related non-Gaussian Diffusion Patterns in the Prefrontal Brain. *J. Reson. Imaging*. 2008; 28: 1345-1350.

Figure 13:
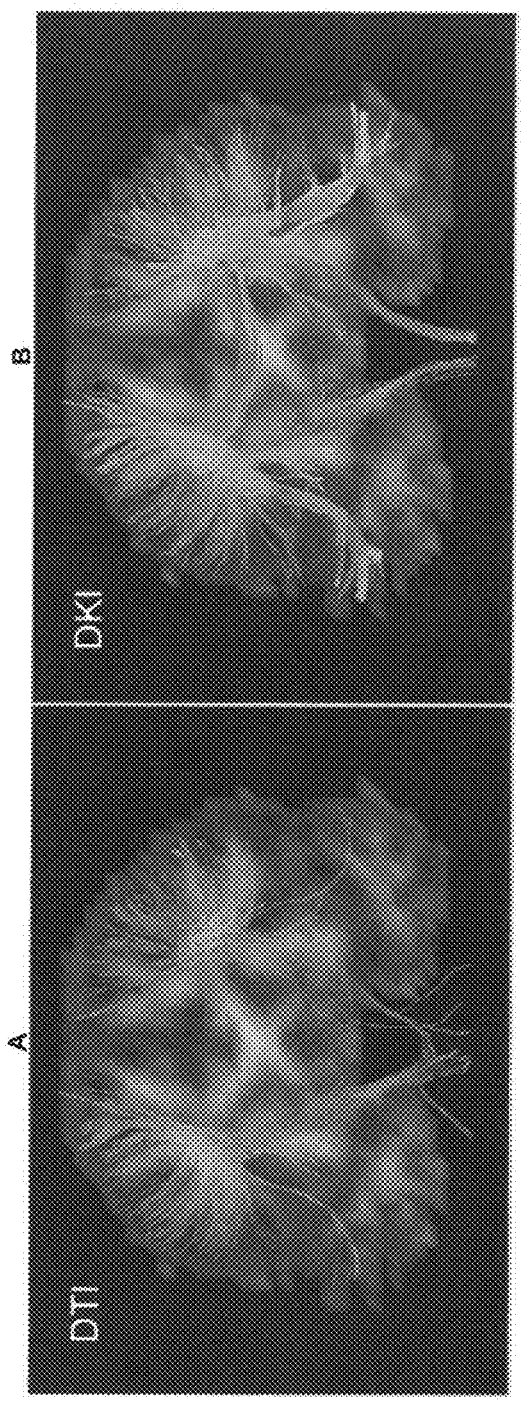
FIG. 13 shows fiber tractographys obtained with (A) a Gaussian dODF and (B) a kurtosis dODF.

FIG. 13 illustrates fiber tractography obtained with the Gaussian and kurtosis dODFs. The kurtosis dODF (DKI-based) tractography utilized a radial weighting power of $\alpha=4$ and generates a richer set of tracks than the Gaussian dODF (DTI-based) tractography. This improvement is a consequence of the ability of the kurtosis dODF to resolve intra-voxel fiber crossings.

From the above description, those skilled in the art will perceive improvements, changes and modifications. Such improvements, changes and modifications are within the skill of one in the art and are intended to be covered by the appended claims.

What is claimed is:

1. A system comprising:
    a non-transitory memory storing computer-executable instructions; and
    a processor that executes the computer-executable instructions to at least:
        receive diffusion magnetic resonance imaging (dMRI) data;
        determine a diffusion tensor (DT) for the dMRI data;
        determine a diffusional kurtosis tensor (DKT) for the dMRI data; and
        determine a kurtosis diffusion orientation distribution function (dODF) for the dMRI data based on the DT and the DKT,
        wherein the kurtosis dODF extends a Gaussian approximation of the DT to include non-Gaussian corrections of the DKT,
        wherein the kurtosis dODF ($\psi_{\alpha,K}(\hat{n})$) is represented by the following equation:

$$\psi_{\alpha,K}(\hat{n}) = \psi_{\alpha,G}(\hat{n})\left\{1 + \frac{1}{24}\sum_{i,j,k,l}[3U_{ij}W_{ijkl}U_{kl} - 6(\alpha+1)U_{ij}W_{ijkl}V_{kl} + (\alpha+1)(\alpha+3)V_{ij}W_{ijkl}V_{kl}]\right\}, \text{ where } V_{ij} \equiv \frac{(U\hat{n})_i(U\hat{n})_j}{\hat{n}^T U\hat{n}},$$

wherein $\psi_{\alpha,G}(\hat{n})$ represents the Gaussian dODF, U represents a dimensionless tensor equal to the product of the mean diffusivity and the inverse of the DT, W represents the DKT, $\alpha$ represents a radial weighting power, i, j, k, and l are indices carried out from 1 to 3, and $\hat{n}$ is a unit direction vector.

2. The system of claim 1, wherein as $\alpha$ increases, the accuracy of the non-Gaussian corrections increases.

3. The system of claim 1, wherein $0 \leq \alpha \leq 5$.

4. The system of claim 3, wherein $3 \leq \alpha \leq 4$.

5. The system of claim 1, wherein the processor further executes the computer-executable instructions to determine a diffusional kurtosis imaging (DKI)-based white matter fiber tractography (WMFT) for the dMRI data based on the kurtosis dODF.

6. The system of claim 5, wherein the WMFT is used to assess a brain connectivity feature.

7. The system of claim 6, wherein the brain connectivity feature comprises at least one of a fiber bundle direction and a fiber bundle crossing.

8. The system of claim 5, wherein the WMFT is used to characterize a neurological disorder,
    wherein the neurological disorder is at least one of Alzheimer's disease, attention deficit hyperactivity disorder, epilepsy, head trauma, schizophrenia, brain cancer, and stroke.

9. A method comprising:
    receiving, by a system comprising a processor, dMRI data;
    determining, by the system, a DT for the dMRI data;
    determining, by the system, a DKT for the dMRI data; and
    determining, by the system, a kurtosis dODF for the dMRI data based on the DT and the DKT,
    wherein the kurtosis dODF extends a Gaussian approximation of the DT to include non-Gaussian corrections of the DKT,
    wherein the kurtosis dODF ($\psi_{\alpha,K}(\hat{n})$) is represented by the following equation:

$$\psi_{\alpha,K}(\hat{n}) = \psi_{\alpha,G}(\hat{n})\left\{1 + \frac{1}{24}\sum_{i,j,k,l}[3U_{ij}W_{ijkl}U_{kl} - 6(\alpha+1)U_{ij}W_{ijkl}V_{kl} + (\alpha+1)(\alpha+3)V_{ij}W_{ijkl}V_{kl}]\right\}, \text{ where } V_{ij} \equiv \frac{(U\hat{n})_i(U\hat{n})_j}{\hat{n}^T U\hat{n}},$$

wherein $\psi_{\alpha,G}(\hat{n})$ represents the Gaussian dODF, U represents a dimensionless tensor equal to the product of the mean diffusivity and the inverse of the DT, W represents the DKT, α represents a radial weighting power, i, j, k, and l are indices carried out from 1 to 3, and $\hat{n}$ is a unit direction vector.

10. The method of claim 9, wherein as α increases, the accuracy of the non-Gaussian corrections increases.

11. The method of claim 9, wherein $0 \leq \alpha \leq 5$.

12. The method of claim 9, wherein $3 \leq \alpha \leq 4$.

13. The method of claim 9, further comprising determining, by the system, a DKI-based WMFT for the dMRI data based on the kurtosis dODF.

14. The method of claim 13, further comprising characterizing, by the system, a neurological disorder based on the WMFT,
wherein the dMRI data is related to a dMRI image of at least a portion of a subject's brain.

15. The method of claim 14, wherein the neurological disorder is at least one of Alzheimer's disease, attention deficit hyperactivity disorder, epilepsy, head trauma, schizophrenia, brain cancer, and stroke.

16. The method of claim 13, further comprising assessing, by the system, a brain connectivity feature based on the WMFT,
wherein the brain connectivity feature comprises at least one of a fiber bundle direction and a fiber bundle crossing.

17. A non-transitory computer-readable storage medium storing instructions executable by an associated processor to perform operations, the operations comprising:

receiving dMRI data of at least a portion of a subject's brain; and determining by the system, a kurtosis dODF for the dMRI data, wherein the kurtosis dODF ($\psi_{\alpha,K}(\hat{n})$) is represented by the following equation:

$$\psi_{\alpha,K}(\hat{n}) = \psi_{\alpha,G}(\hat{n}) \left\{ 1 + \frac{1}{24} \sum_{i,j,k,l} [3 U_{ij} W_{ijkl} U_{kl} - 6(\alpha+1) U_{ij} W_{ijkl} V_{kl} + (\alpha+1)(\alpha+3) V_{ij} W_{ijkl} V_{kl}] \right\}, \text{ where } V_{ij} \equiv \frac{(U\hat{n})_i (U\hat{n})_j}{\hat{n}^T U \hat{n}},$$

wherein $\omega_{\alpha,G}(\hat{n})$ represents the Gaussian dODF, U represents a dimensionless tensor equal to the product of the mean diffusivity and the inverse of the DT, W represents the DKT, α represents a radial weighting power, i, j, k, and l are indices carried out from 1 to 3, and $\hat{n}$ is a unit direction vector.

18. The non-transitory computer-readable storage medium of claim 17, wherein the operations further comprise determining a DKI-based WMFT for the dMRI data based on the kurtosis dODF.

* * * * *